US012048761B2

United States Patent
Behar-Cohen et al.

(10) Patent No.: US 12,048,761 B2
(45) Date of Patent: Jul. 30, 2024

(54) METHODS AND PHARMACEUTICAL COMPOSITIONS FOR THE TREATMENT OF RETINAL CAPILLARY NON-PERFUSION

(71) Applicants: INSERM (INSTITUT NATIONAL DE LA SANTÉ ET DE LA RECHERCHE MÉDICALE), Paris (FR); UNIVERSITÉ PARIS DESCARTES, Paris (FR); UNIVERSITÉ PARIS DIDEROT—PARIS 7, Paris (FR); FONDATION ASILE DES AVEUGLES, Lausanne (CH); SORBONNE UNIVERSITÉ, Paris (FR)

(72) Inventors: Francine Behar-Cohen, Paris (FR); Patricia Crisanti-Lassiaz, Paris (FR)

(73) Assignees: INSERM (INSTITUT NATIONAL DE LA SANTÉ ET DE LA RECHERCHE MEDICALE), Paris (FR); UNIVERSITÉ PARIS DESCARTES, Paris (FR); UNIVERSITÉ PARIS DIDEROT—PARIS 7, Paris (FR); FONDATION ASILE DES AVEUGLES, Lausanne (CH); SORBONNE UNIVERSITÉ, Paris (FR)

(*) Notice: Subject to any disclaimer, the term of this patent is extended or adjusted under 35 U.S.C. 154(b) by 0 days.

(21) Appl. No.: 15/765,854

(22) PCT Filed: Oct. 12, 2016

(86) PCT No.: PCT/EP2016/074468
§ 371 (c)(1),
(2) Date: Apr. 4, 2018

(87) PCT Pub. No.: WO2017/064119
PCT Pub. Date: Apr. 20, 2017

(65) Prior Publication Data
US 2018/0296474 A1    Oct. 18, 2018

(30) Foreign Application Priority Data
Oct. 13, 2015  (EP) ...................... 15306618

(51) Int. Cl.
*A61K 31/437* (2006.01)
*A61K 9/00* (2006.01)
(Continued)

(52) U.S. Cl.
CPC .......... *A61K 9/0051* (2013.01); *A61K 9/0048* (2013.01); *A61K 31/437* (2013.01);
(Continued)

(58) Field of Classification Search
CPC ...................................................... A61P 27/02
See application file for complete search history.

(56) References Cited

U.S. PATENT DOCUMENTS

| 5,869,079 A * | 2/1999 | Wong ............. A61F 9/0017 424/426 |
| 7,893,050 B2 * | 2/2011 | Fong ............. A61K 31/137 514/211.07 |
| 2014/0378441 A1 | 12/2014 | Ishibashi et al. |

FOREIGN PATENT DOCUMENTS

| EP | 1378247 A1 | 1/2004 |
| WO | 97/23222 A1 | 7/1997 |
| WO | 2015/029923 A1 | 3/2015 |

OTHER PUBLICATIONS

Campochiaro, Vascular Endothelial Growth Factor Promotes Progressive Retinal Nonperfusion in Patients with Retinal Vein Occlusion, Ophthalmology, 2013, 120(4), pp. 795-802. (Year: 2013).*
(Continued)

*Primary Examiner* — Clinton A Brooks
*Assistant Examiner* — Andrew P Lee
(74) *Attorney, Agent, or Firm* — WCF IP

(57) ABSTRACT

The present invention relates to methods and pharmaceutical compositions for the treatment of retinal capillary non-perfusion. In particular, the present invention relates to a method of treating retinal capillary non-perfusion in a sub-
(Continued)

Figure 1:
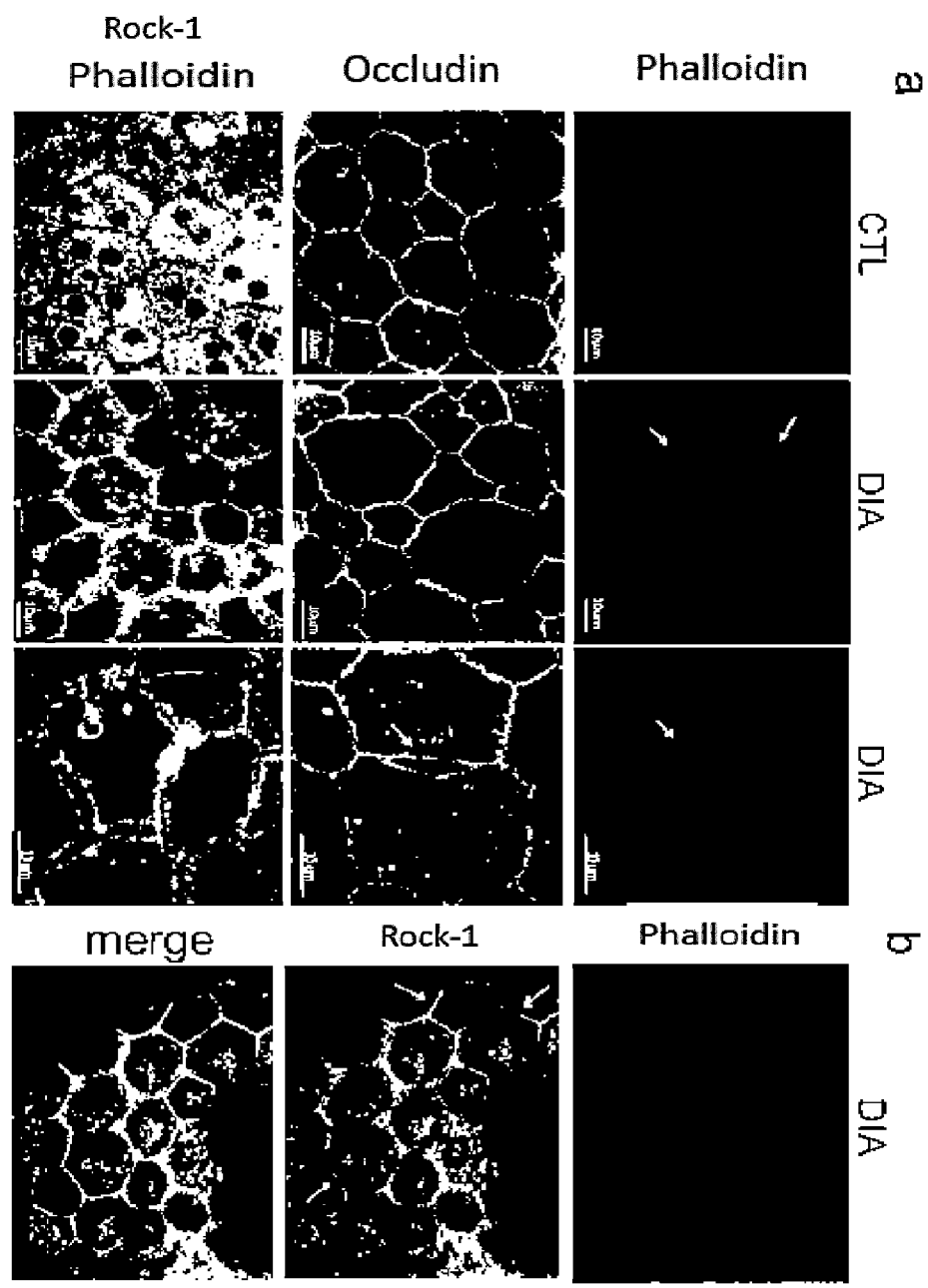

ject in need thereof comprising administering to the subject a therapeutically effective amount of a ROCK inhibitor.

7 Claims, 15 Drawing Sheets

(51) Int. Cl.
    *A61K 31/4409*     (2006.01)
    *A61K 31/551*     (2006.01)
    *A61P 27/02*     (2006.01)

(52) U.S. Cl.
    CPC ........ *A61K 31/4409* (2013.01); *A61K 31/551* (2013.01); *A61P 27/02* (2018.01)

(56) References Cited

OTHER PUBLICATIONS

Arita, Rho Kinase Inhibition by Fasudil Ameliorates Diabetes-Induced Microvascular Damage, Diabetes, 2009, 58, pp. 215-226 (Year: 2009).*
Zhang, Protective Factors in Diabetic Retinopathy: Focus on Blood-Retinal Barrier, Discovery Medicine, 2014, 18(98), pp. 105-112 (Year: 2014).*
Vujosevic et al., Retinal Layers Changes in Human Preclinical and Early Clinical Diabetic Retinopathy Support Early Retinal Neuronal and Müller Cells Alterations, Journal of Diabetes Research, 2013, pp. 1-7 (Year: 2013).*
Dai et al., Rho kinase signaling and cardiac physiology, 2018, 1, pp. 14-20 (Year: 2018).*
Danziger, Automated site-directed drug design: a general algorithm for knowledge acquisition about hydrogen-bonding regions at protein surfaces, Proc. R. Soc. Lond., 1989, 236,pp. 101-113 (Year: 1989).*
Jianglong Yu et al: "Original Article Fasudil alleviates traumatic optic neuropathy by inhibiting Rho signaling pathway", Int J Clin Exp Med, Jan. 1, 2015, pp. 13377-13382.
R. Arita et al: "Rho Kinase Inhibition by Fasudil Ameliorates Diabetes-Induced Microvascular Damage", Diabetes, vol. 58, No. 1, Jan. 1, 2009, pp. 215-226.
Ramin Nourinia et al: "Intravitreal Fasudil Combined with Bevacizumab for Treatment of Refractory Diabetic Macular Edema; a Pilot Study Introduction", Original Article Journal of Ophthalmic and Vision Research, Jan. 1, 2013.
Tamotsu Yokota et al: "Involvement of the Rho/Rho Kinase Signaling Pathway in Platelet-Derived Growth Factor BB-induced Vascular Endothelial Growth Factor Expression in Diabetic Rat Retina", Japanese Journal of Ophthalmology; The Official English-Language Journal of the Japanese Ophthalmological Society, Springer-Werlag, TO, vol. 51, No. 6, Dec. 21, 2007, pp. 424-430.
Akira Hirata et al: "Y-27632, a Rho-associated protein kinase inhibitor, attenuates neuronal cell death after transient retinal ischemia", Graefe's Archive for Clinical and Experimental Ophthalmology; Incorporating German Journal of Ophthalmology, Springer, Berlin, DE, vol. 246, No. 1, Aug. 31, 2007, pp. 51-59.
Meng Q-Q et al: "Protection of y-39983 preconditioning from retinal ischemia-reperfusion injury in rats", EMBASE, Jul. 1, 2013, XP002741234.
Masoud A. Fard et al. : "The Effect of Intravitreal Rock Inhibitor (H1152p) on Inflammation, RGC Loss and Axonal Regeneration in Experimental Model of Adult Rodent Anterior Ischemic Optic Neuropathy", Investigate Ophthalmology and Visual Science, vol. 52, Apr. 1, 2011.
Yu Jianlong et al: "Fasudil, a Rho-Associated Protein Kinase Inhibitor, Attenuates Traumatic Retinal Nerve Injury in Rabbits", Journal of Molecular Neuroscience, Birkhaeuser, Cambrigde, MA, US, vol. 58, No. 1, Dec. 3, 2015, pp. 74-82.

\* cited by examiner

Figure 2C:
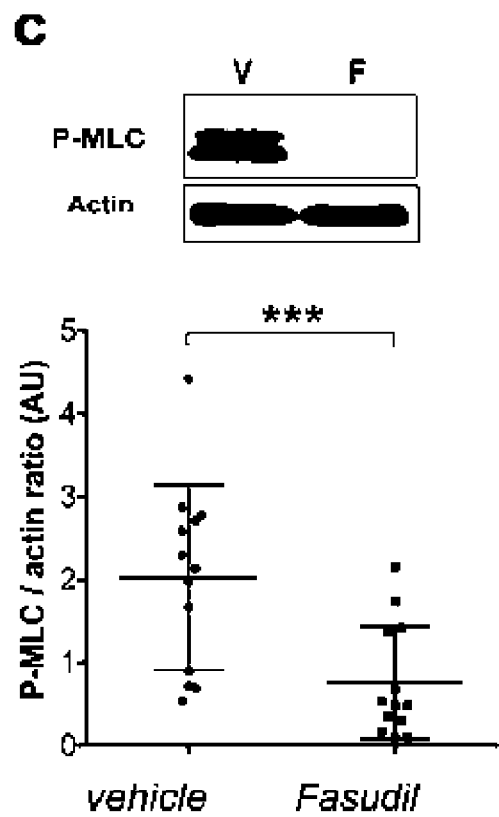

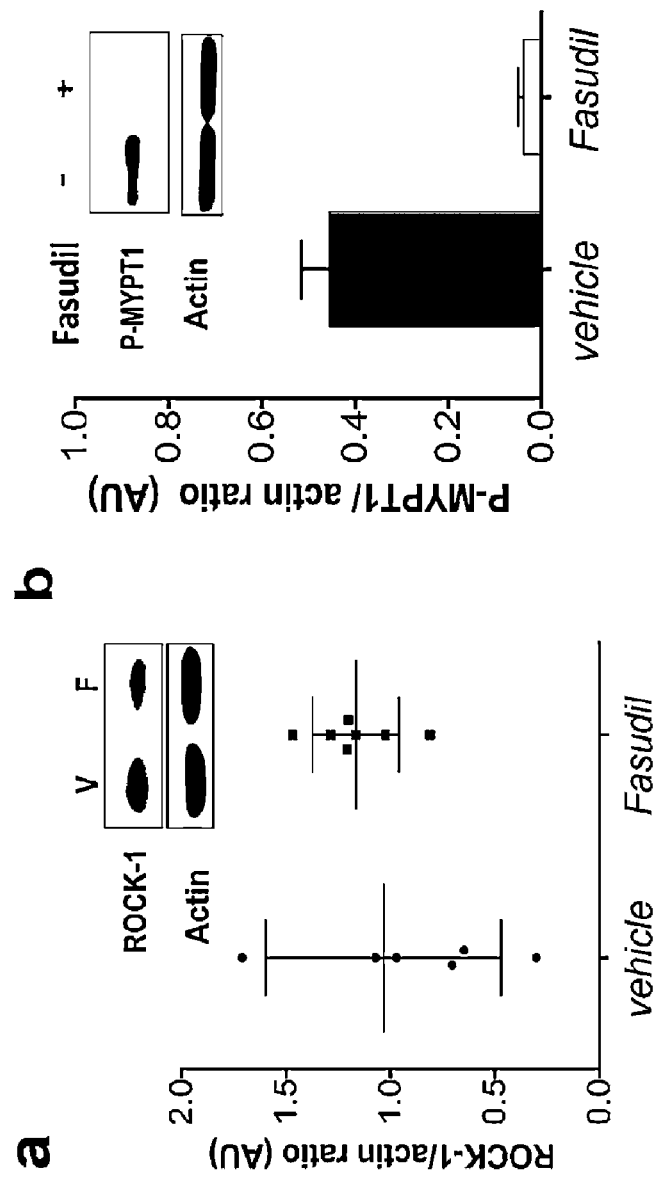
FIG. 2A-B

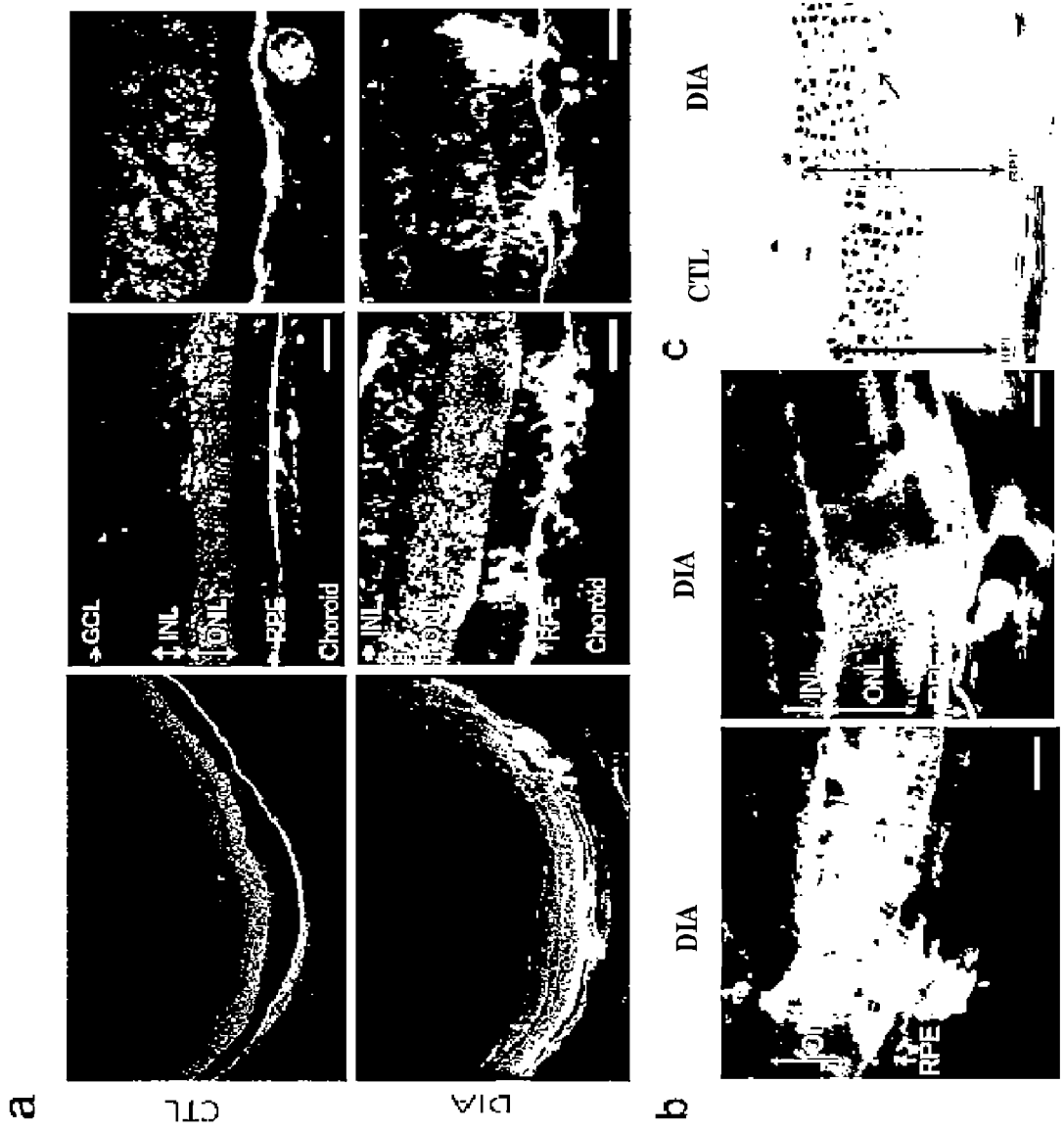
FIG. 4A-C

Figures 5A-B

METHODS AND PHARMACEUTICAL COMPOSITIONS FOR THE TREATMENT OF RETINAL CAPILLARY NON-PERFUSION

FIELD OF THE INVENTION

The present invention relates to methods and pharmaceutical compositions for the treatment of retinal capillary non-perfusion.

BACKGROUND OF THE INVENTION

The chronic development of a state of retinal ischemia in pathologies such as diabetic retinopathy, retinopathy engendered by radiation and damage consecutive to a venous occlusion results in a disturbance of the depolarization of the cellular membrane, which entails, over time, an irreversible destruction of the retina. Thus, retinal ischemia is observed in the clinic in acute situations such as arterial or venous occlusions of the retina, after radiation and also in chronic pathologies such as diabetic retinopathy, premature infant retinopathy, and inflammatory diseases and hemopathies that lead to retinal damage even resulting in a number of cases in a total degeneration of the retina. For instance, diabetic retinopathy (DR) is the leading cause of blindness amongst working age individuals in western countries, representing a major public health concern [1]. Vision loss with progressive DR arises through two major mechanisms, macular oedema and retinal ischemia with subsequent neovascular and haemorrhagic complications. Chronic hyperglycaemia induces neurodegeneration, inflammation, glial activation that ultimately result in the breakdown of the blood retinal barrier (BRB). The inner blood-retinal barrier in retinal capillaries is composed of a tight junction endothelium layer, and the outer retinal barrier is formed by the tight junction retinal pigment epithelium (RPE). These two retinal barriers tightly control all exchange between the retina and systemic circulation while maintaining together with retinal Müller cells, the hydro-ionic homeostasis. DR has been considered primarily as a microangiopathy, used clinically to screening and grading of the disease stage [2]. However novel exploration methods, have demonstrated that outer retinal barrier breakdown and neuro-degeneration precede the retinal vascular observable changes [3-5]. To date, therapeutic options for DR have included laser photocoagulation of the ischemic peripheral retina to avoid neovascularization and intraocular injection of anti-oedematous drugs (anti-VEGF and corticoids) to reduce macular oedema [6]. No treatment is currently available when ischemia affects the macula and irreversibly alters the central vision. Clinical management of diabetic retinopathy has succeeded to significantly reduce the number of severe complications but retinal ischemia remains one of the major causes of vision loss. Two closely related Rho kinases, ROCK1 and ROCK2, have been identified as key downstream effectors of Rho GTPases, which in turn contribute to multiple cytoskeleton functions [7]. Both kinases have overlapping cellular functions, however in polarized cells ROCK-1 is reportedly predominant [8-10]. To date abnormal ROCK-1 activation has been shown in various diseases such as hypertension [11, 12], coronary and cerebral vasospasm [13, 14], atherosclerosis [15], stroke [16], pulmonary hypertension [17, 18], and cardiovascular diseases [19, 20]. In diabetic retinopathy, the Rho/ROCK-1 pathway is thought to be involved in the development of retinal microangiopathy, neovascularization and tractional retinal detachment [21]. Fasudil is a Rho-kinase inhibitor that has demonstrated remarkable acute vasodilator, neuroprotective, and anti-inflammatory properties not only in experimental models but also in clinical trials [21-25]. Positive results were recently reported in a pilot study where fasudil was combined with intravitreal bevacizumab (anti-VEGF) for patients with macular oedema resistant to anti VEGF alone [26].

SUMMARY OF THE INVENTION

The present invention relates to methods and pharmaceutical compositions for the treatment of retinal capillary non-perfusion. In particular, the present invention is defined by the claims.

DETAILED DESCRIPTION OF THE INVENTION

The inventors hypothesized that Rho/Rock1 pathway contributes to cytoskeleton remodeling in endothelial cells and retinal pigment epithelial cells, subsequently altering barriers function and capillary perfusion. They used 12 months old Goto-Kakizaki (GK) type 2 diabetic rat and human diabetic retina. Rho/Rhock1 pathway activation were analysed in retinal endothelial cells and in pigment epithelial cells (RPE) through their sub cellular localization in rats and humans and the phosphorylation of its substrates. Its inhibition by Fasudil was tested in vivo in rats on barriers permeability and capillary perfusion. In diabetic rats, Rock1 is activated in retinal endothelial cells and RPE cells as shown by its cytoplasmic internalization and MYTP1 activation. Similar location was found in human diabetic retina. Rock1 activation induced severe cytoskeleton remodeling, cell size polydispersity, apical constriction and membrane blebs leading to junction opening in RPE cells and to capillary closure in retinal capillaries. Fasudil partially restored barrier function and retinal perfusion and reduce retinal VEGF expression. Rho/Rock1 pathway is thus a major player in diabetic-induced barrier and perfusion alterations in the retina. Its local ocular inhibition could have beneficial effects in the treatment of retinal ischemia.

Accordingly the present invention relates to a method of treating retinal capillary non-perfusion in a subject in need thereof comprising administering to the subject a therapeutically effective amount of a ROCK inhibitor.

In some embodiments, the subject suffers from retinal ischemia. The term "retinal ischemia" has its general meaning in the art and refers to those conditions wherein the blood supply to the retinal cells is impaired, resulting in a deficiency of oxygenation to retinal tissue. The term includes macular ischemia.

In some embodiments, the subject suffers from retinal ischemia secondary to an eye disease selected from the group consisting of Behcet's disease; diabetic uveitis; edema, such as macular edema, cystoid macular edema and diabetic macular edema; multifocal choroiditis; retinal vein occlusion, diabetic retinopathy, retinal arterial occlusive disease, and radiation retinopathy.

In some embodiments, the subject suffers from macular ischemia that is associated with macular edema. Macular ischemia is a major cause of irreversible vision acuity loss and decreased contrast sensitivity in patients with diabetic retinopathy.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein the term "RhoA kinase" or "ROCK" has its general meaning in the art. ROCK is a member of the serine-threonine protein kinase family. ROCK exists in two isoforms, ROCK1 and ROCK2 (T. Ishizaki et al, EMBO J., 19%, 15, 1885-1893). ROCK has been identified as an effector molecule of RhoA, a small GTP-binding protein (G protein) that plays a key role in multiple cellular signaling pathways.

As used herein, the term "ROCK inhibitor" refers to a natural or synthetic compound which inhibits ROCK1, and/or ROCK2 activity. In a particular embodiment the inhibitor is selective. The selective ROCK inhibiting compounds are not limited to a particular manner of selective ROCK inhibition. For example, in some embodiments, one or more of the selective ROCK inhibiting compounds selectively inhibit ROCK1 activity over ROCK2 activity. For example, in some embodiments, one or more of the selective ROCK inhibiting compounds selectively inhibit ROCK2 activity over ROCK1 activity. Moreover, in some embodiments, one or more of the selective ROCK inhibiting compounds selectively inhibit both ROCK1 activity and ROCK2 activity with similar capability.

ROCK inhibitors are well known in the art. For example, isoquinoline derivatives, especially fasudil, are typical ROCK inhibitors. Fasudil (hexahydro-1-(5-isoquinolylsulfonyl)-1H-1,4-di-azepime), also named as HA-1077, is an isoquinoline sulfonamide derivative and the only clinically available ROCK inhibitor codeveloped by Asahi Kasei of Japan and Department of Pharmacology of Nagoya University. Hydroxyfasudil is an active metabolite of fasudil in vivo, which has higher affinity to ROCK than Fasudil. Another isoquinoline derivative, H-1152P, is optimized on the basis of fasudil. Through competitively binding to the ATP binding pocket, Y-27632, another type of ROCK inhibitor, inhibits both ROCK1 and ROCK2. Optimization of these compounds leads to a more potent ROCK inhibitor, Y-39983, which is benefit for the treatment of the glaucoma (Kubo T, Yamaguchi A, Iwata N, The therapeutic effects of Rho-ROCK inhibitors on CNS disorders. Ther Clin Risk Manag 2008; 4(3):605-15). SLx-2119, a ROCK2-specific inhibitor, has recently been developed (Boerma M, Fu Q, Wang J, Comparative gene expression profiling in three primary human cell lines after treatment with a novel inhibitor of Rho kinase or atorvastatin. Blood Coagul Fibrinolysis 2008; 19(7):709-18). A series of fasudil analogs were synthesized and their selectivity and inhibitory activity against ROCK were evaluated (Satoh N, Toyohira Y, Itoh H, Stimulation of norepinephrine transporter function by fasudil, a Rho kinase inhibitor, in cultured bovine adrenal medullary cells. Naunyn Schmiedebergs Arch Pharmacol 2012; 385(9):921-31; Nakabayashi S, Nagaoka T, Tani T, Retinal arteriolar responses to acute severe elevation in systemic blood pressure in cats: role of endothelium-derived factors. Exp Eye Res 2012; 103:63-70; Sun X, Minohara M, Kikuchi H, The selective Rho-kinase inhibitor Fasudil is protective and therapeutic in experimental autoimmune encephalomyelitis. J Neuroimmunol 2006; 180(1-2):126-34; Yu J Z, Ding J, Ma C G, Therapeutic potential of experimental autoimmune encephalomyelitis by Fasudil, a Rho kinase inhibitor. J Neurosci Res 2010; 88(8):1664-72; Hou S W, Liu C Y, Li Y H, Fasudil ameliorates disease progression in experimental autoimmune encephalomyelitis, acting possibly through anti-inflammatory effect. CNS Neurosci Ther 2012; 18(11):909-17; LoGrasso P V, Feng Y. Rho kinase (ROCK) inhibitors and their application to inflammatory disorders. Curr Top Med Chem 2009; 9(8):704-23; Engel J Jr. A proposed diagnostic scheme for people with epileptic seizures and with epilepsy: report of the ILAE Task Force on Classification and Terminology. Epilepsia 2001; 42(6):796-803; Fisher R S, van Emde Boas W, Blume W, Epileptic seizures and epilepsy: definitions proposed by the International League Against Epilepsy (ILAE) and the International Bureau for Epilepsy (IBE). Epilepsia 2005; 46(4): 470-2. Inan S, Buyukafsar K. Antiepileptic effects of two Rho-kinase inhibitors, Y-27632 and fasudil, in mice. Br J Pharmacol 2008; 155(1):44-51; Meihui Chen, Anmin Liu, Ying Ouyang, Yingjuan Huang, Xiaojuan Chao, Rongbiao Pi Fasudil and its analogs: a new powerful weapon in the long war against central nervous system disorders? Expert Opinion on Investigational Drugs April 2013, Vol. 22, No. 4, Pages 537-550). Other examples of ROCK inhibitors include those described in the international patent publications WO98/06433, WO00/09162, WO00/78351, WO01/17562, WO02/076976, EP1256574, WO02/100833, WO03/082808, WO2004/009555, WO2004/024717, WO2004/108724, WO2005/003101, WO20Q5/035501, WO2005/035503, WO2005/035506, WO2005/058891, WO2005/074642, WO2005/074643, WO2005/Q80934, WO2005/082367, WO2005/082890, WO2005/097790, WO2005/100342, WO2005/103050, WO2005/105780, WO2005/108397, WO2006/044753, WO2006/051311, WO2006/057270, WO2006/058120, WO2006/072792WO2011107608A1, and WO2007026920A2.

By a "therapeutically effective amount" is meant a sufficient amount of the ROCK inhibitor for the treatment of retinal capillary non-perfusion at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the ROCK inhibitor for the symptomatic adjustment of the dosage to the subject to be treated. A medicament typically contains from about 0.01 mg to about 500 mg of the ROCK inhibitor, preferably from 1 mg to about 100 mg of the ROCK inhibitor. An effective amount of the drug is ordinarily supplied at a dosage level from 0.0002 mg/kg to about 20 mg/kg of body weight per day, especially from about 0.001 mg/kg to 7 mg/kg of body weight per day.

The ROCK inhibitor is typically combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In some embodiments, the ROCK inhibitor is administered to the subject via the intravitreous route.

In some embodiments, the ROCK inhibitor of the present invention is administered to the subject through a biodegradable ocular implant. The implants can be formed in manner that the ROCK inhibitor is homogenously distributed or dispersed throughout the biodegradable polymer matrix. Additionally, the implants can be formed to release the ROCK inhibitor into an ocular region of the eye over various time periods. Thus, the ROCK inhibitor can be released from implants made according to the present invention for a period of time of for example, 30-200 days. The ROCK inhibitor can comprise from about 10% to about 90% by weight of the implant. In some embodiments, the agent is from about 40% to about 80% by weight of the implant. In some embodiments, the ROCK inhibitor can be homogeneously dispersed in the biodegradable polymer of the implant. The implant can be made, for example, by a sequential or double extrusion method. The selection of the biodegradable polymer used can vary with the desired release kinetics, patient tolerance, the nature of the disease to be treated, and the like. Polymer characteristics that are considered include, but are not limited to, the biocompatibility and biodegradability at the site of implantation, compatibility with the ROCK inhibitor of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. Biodegradable polymers which can be used include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked. If crosslinked, they are usually not more than lightly crosslinked, and are less than 5% crosslinked, usually less than 1% crosslinked. Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In some embodiments, 25/75 PLGA and/or 50/50 PLGA copolymers are used. The biodegradable ocular implants can also include additional hydrophilic or hydrophobic compounds that accelerate or retard release of the ROCK inhibitor. Additionally, release modulators such as those described in U.S. Pat. No. 5,869,079 can be included in the implants. The amount of release modulator employed will be dependent on the desired release profile, the activity of the modulator, and on the release profile of the ROCK inhibitor in the absence of modulator. Where the buffering agent or release enhancer or modulator is hydrophilic, it may also act as a release accelerator. Hydrophilic additives act to increase the release rates through faster dissolution of the material surrounding the drug particles, which increases the surface area of the drug exposed, thereby increasing the rate of drug diffusion. Similarly, a hydrophobic buffering agent or enhancer or modulator can dissolve more slowly, slowing the exposure of drug particles, and thereby slowing the rate of drug diffusion. The release kinetics of the implants of the present invention can be dependent in part on the surface area of the implants. A larger surface area exposes more polymer and ROCK inhibitor to ocular fluid, causing faster erosion of the polymer matrix and dissolution of the ROCK inhibitor particles in the fluid. Therefore, the size and shape of the implant may also be used to control the rate of release, period of treatment, and ROCK inhibitor concentration at the site of implantation. At equal ROCK inhibitor loads, larger implants will deliver a proportionately larger dose, but depending on the surface to mass ratio, may possess a slower release rate. For implantation in an ocular region, the total weight of the implant preferably ranges, e.g., from about 200-15000 [mu]g, usually from about 1000-5000 [mu]g. In some embodiments, the total weight of the implant is about 1200 to about 1,800 [mu]g. In some embodiments, the total weight of the implant is about 2400 to about 3,600 [mu]g. The implants of the invention are typically solid, and may be formed as particles, sheets, patches, plaques, films, discs, fibers, rods, and the like, or may be of any size or shape compatible with the selected site of implantation, as long as the implants have the desired release kinetics and deliver an amount of ROCK inhibitor that is therapeutic for the intended medical condition of the eye. The upper limit for the implant size will be determined by factors such as the desired release kinetics, toleration for the implant at the site of implantation, size limitations on insertion, and ease of handling. For example, the vitreous chamber is able to accommodate relatively large rod-shaped implants, generally having diameters of about 0.05 mm to 3 mm and a length of about 0.5 to about 10 mm. In yet a further variation, other implants having variable geometries but approximately similar volumes may also be used. The biodegradable implants can be inserted into the eye by a variety of methods, including placement by forceps, by trocard, or by other types of applicators, after making an incision in the sclera. In some embodiments, a trocard or applicator may be used without creating an incision. In some embodiments, a hand held applicator is used to insert one or more biodegradable implants into the eye. The hand held applicator typically comprises an 18-30 GA stainless steel needle, a lever, an actuator, and a plunger. Suitable devices for inserting an implant or implants into a posterior ocular region or site includes those disclosed in U.S. patent application Ser. No. 10/666,872.

The invention will be further illustrated by the following figures and examples. However, these examples and figures should not be interpreted in any way as limiting the scope of the present invention.

FIGURES

FIG. 1. Effect of diabetes on rat and human diabetic RPE flatmounts. (a) Rat RPE cell cytoskeleton was studied by phalloidin staining, tight junction integrity was assessed by occludin staining. ROCK-1 immunolocalization was assessed by a Rock-1 phalloidin costaining. (b) ROCK-1 immunolocalization in humans was assessed by a Rock-1 phalloidin costaining. Scale bar=10 µm, n=7 for each experiment.

FIG. 2. Effect of FASUDIL intravitreal treatment on diabetic outer blood retinal barrier. Western blotting analyses were performed to assess ROCK activity by an immunoblot kit that quantifies the level of phosphorylation of a recombinant form of MYPT1 a ROCK substrate (a); ROCK1 protein level (b); p-MLC protein level (c). Immunolocalization of ROCK1 and P-MLC on RPE cell flatmounts. n=6-12; ***=p value<0.001

Figure 3:
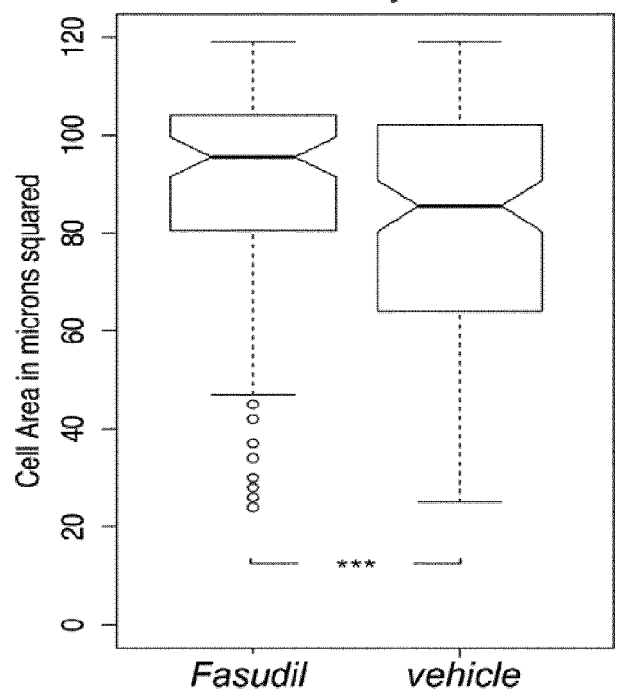

FIG. 3. Quantitative analysis of RPE cell layer morphology. To show the effect of FASUDIL on the cell size, a boxplot summarising the distribution of small cells in Fasudil and vehicle treated eyes in the diabetic type GK rat model is shown. The Fasudil treated retina had significantly less small cells than the retina treated with vehicle n=7 for each experiment; ***=p value<0.001

FIG. 4. Analysis of diabetic outer retinal barrier permeability and outer retinal oedema. Whole retinal cryosections were obtained from diabetic and control rats killed two hours after an intravenous injection 150 KDa FITC-labelled molecules. Leakage within the retina at RPE break points were qualitatively studied (a) as well as retinal infiltration in all other retinal layers (b). Whole retinal semithin sections were performed to evaluate extracellular oedema (c). Whole retinal cryosections from FASUDIL intravitreal injected rats were qualitatively studied to evaluate the presence of RPE break points (d). Neural retina corrected total fluorescence was quantified by image J software (e). n=5-6; **=p value<0, 01.

Figure 5C:
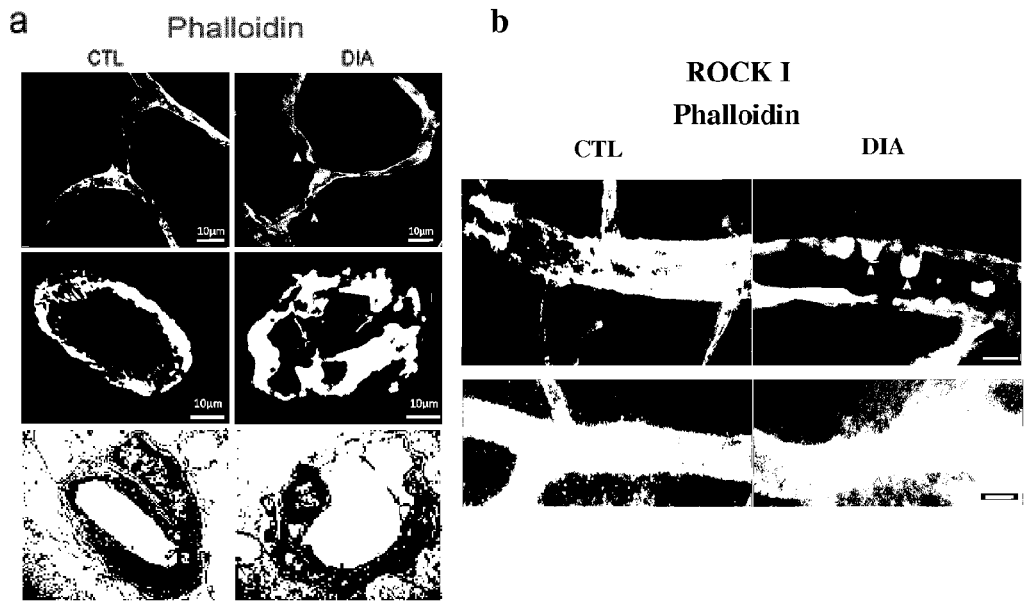
Figure 5C:
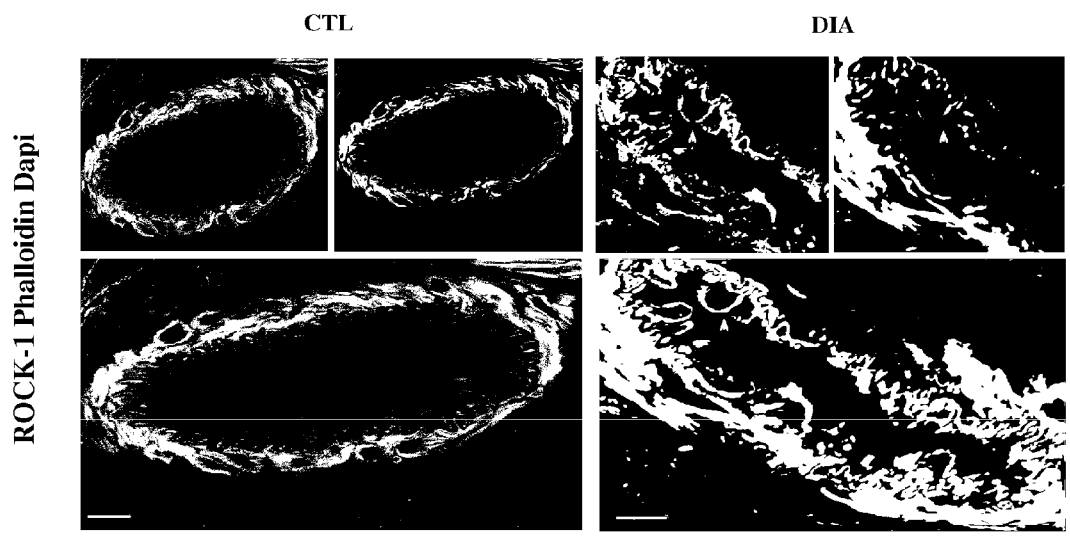

FIG. 5. Effect of ROCK activation in retinal blood vessels during diabetes. (a) Phalloidin immunostaining in diabetic rat retinal arterioles of flat mounted retinas (FIG. 5a, upper row), and cryosections (FIG. 5a, middle row) and TEM ultrathin section (FIG. 5a, lower row). (b) Neural retina flatmounts of diabetic rat showing ROCK and phalloidin immunostaining in retinal arterioles. (c) Transversal cryosections of human inner blood retinal network arterioles were studied by phalloidin and ROCK1 labelling.

FIG. 6. Effect of FASUDIL on retinal capillaries during diabetic retinopathy. (a) Automated detection of retinal capillary network surface performed on retinal flatmounts stained by an immunofluorescent lectin (first row) to highlight the vessel walls in vehicle and Fasudil treated rats. Qualitative assessment is aided by a colour coding (second raw) where small vessels are represented by cold colours (blue) and larger arterioles by hot colours (red). (b) Scatter plot showing the quantification of the total surface of the retinal capillary network in vehicle and Fasudil treated rats. n=4-5; *=p value<0, 05

Figure 7A:
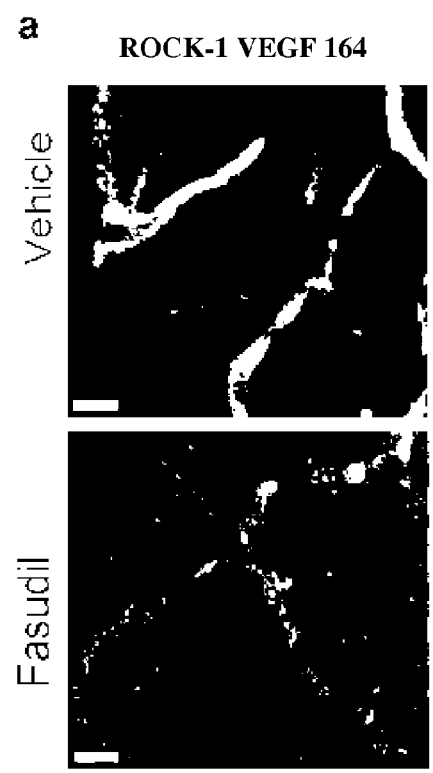
Figure 7B:
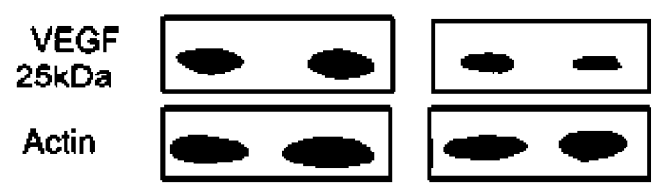
Figure 7B:
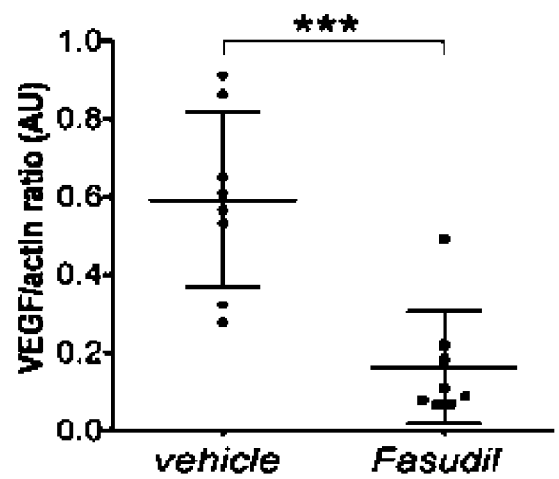

FIG. 7. Effect of FASUDIL on retinal VEGF. (a) VEGF immunostaining on retinal flatmounts in vehicle and treated rats. (b) Scatter plot of VEGF western blot results in neural retina samples of vehicle and treated rats. n=8; ***=p value<0,001

FIG. 8. Effect of intravitreal fasudil on GK rat retinal vessel dilation
  A. Vascular diameter before and after fasudil treatment determined a vasodilation ratio showing significant effect of fasudil on retinal vessel diameter (p<0.05).
  B. The retinal surface coverage by small vessels was significantly increased in fasudil treated GK rats as compared to vehicle treated GK rats (n=4-5 per group, p<0.05) consistent with a vasodilation of retinal capillaries.
  C. Western blot showed a significant decrease in the VEGF-164 level in the neural retina of fasudil treated GK rats as compared to vehicle treated GK rats, suggesting decreased retinal hypoxia in fasudil treated retina (n=8 per group). *=p value<0, 05; =p value<0, 01*=p value<0,001.

EXAMPLE

Methods
Ethical Issues

Animal experiments followed the European Community guidelines and were approved by the local Ethical Committees and were registered (Ce5/2012/085, Ce5/2012/080, and Ce5-2009-034). In accordance with the "3R" rules, experiments were designed to reduce the number of animals. The GK model being well characterized in our laboratory, we could determine the minimal number of animals required for each experiment (10 animals per group at the maximum) and the most relevant time points for animals to be killed.

Human Ocular Tissues

Two ocular globes from patients enucleated for recurrent peripheral melanoma more than 5 years after protontherapy were used. One patient, with type 2 diabetes for 23 years (female, 67 years-old), who had suffered from diabetic macular oedema and had several systemic diabetic complications (diabetic nephropathy with end-stage renal failure and dialysis and peripheral neuropathy). The second eye was from a non-diabetic patient (female, 56 years-old) presenting a minimal sub foveal detachment (<30 µm) and elongated segment. The enucleated eyes were sectioned and the anterior part (including retina up to the equator) was used for classical pathologic examination. The posterior retina of both eyes were used for immunohistochemistry on cryosections. Due to the enucleation procedure, fresh tissues were available for analysis.

Animal Model

Goto-Kakizaki (GK) rats (Taconic Europe, Denmark), a Wistar strain of non-obese, type 2 diabetes, were studied at 12 months of age. Non-fasting blood glucose was measured using Accutrend GC and Accu-check compact equipment (Roche) and HbA1c was measured with A1C NOW+ multitest system (Bayer, Germany). A plasma glucose level>250 mg/dl (14 mmol/l) defined the diabetic status. In contrast to control Wistar rats, GK rats develop hyperglycaemia at approximately 14 weeks of age (Table 1). Control age-matched Wistar rats (WS) were normoglycaemic.

Intravitreal Injection of the ROCK Inhibitor, Fasudil

For intravitreous injections, diabetic rats were anesthetized with an intraperitoneal injection of pentobarbital (40 mg/kg Nembutal, Abbot, Saint-Remy sur Avre, France) and pupils were dilated with a topically applied drop of 5% tropicamide (Ciba Vision, Toulouse, France), and locally anesthetized with a drop of 1% tetracaine (Ciba Vision). Three consecutive injections, of Fasudil at a concentration of 20 M or vehicle were performed, at 48 hours interval under a surgical microscope, using a 30-gauge needle (Microfine: Becton Dickinson, Meylan, France as described previously [29-31]). Animals were sacrificed 48 hours following the administration of 3 intra-vitreous injections of 20 µM of Fasudil, each injection was 2 days apart.

Immunohistochemistry on Retina Cryosections and on Retinal Flat-mounts of Neural Retina or RPE/Choroid For sections, rat eyes were enucleated, fixed in 4% paraformaldehyde, cryoprotected with sucrose (20% in PBS) and embedded in optimal cutting-temperature compound (Tissue-Tek; Miles Inc., Bayer Diagnostics, Puteaux, France), frozen in liquid nitrogen and stored at −80° C. Cryostat frozen sections (thickness of 10 µm) (Leica CM 3050S, Wetzlar, Germany) were performed and mounted on gelatin-coated slides for immunohistochemical analysis.

For flatmounts, after enucleation, ocular globes were fixed in 4% paraformaldehyde (PFA) for 15 min at room temperature and sectioned at the limbus; anterior segments were discarded. Neural retinas and RPE/choroids were fixed separately for additional 15 min in acetone at −20° C. Specimens were then incubated overnight at 4° C. with primary antibodies diluted in PBS supplemented with 10% foetal calf serum (FCS) and 0.1% Triton X-100. The list of antibodies used in this study are provided in Table 2. Immunohistochemistry was repeated at least 7 times on 7 different animals for each group. Negative controls were obtained by staining procedures that omitted the primary antibody (data not shown).

Western Blotting

RPE/choroid and neural retina were homogenized in a lysis buffer (50 mM Mops, 50 mM Trisbase, 0.1%, SDS 1 mM EDTA PH 7.7) containing a protease inhibitor cocktail (Roche, France). Protein concentration was determined using a (Pierce BCA protein assay kit Thermo Scientific Rockford USA) (20-40 µg) were subjected to SDS-PAGE on Nupage 4-12% Bis-Tris gel electrophoresis, and electroblotted onto nitrocellulose membranes (Optitran BA-S 83 GE Healthcare Life Science Whatman). Membranes were incubated with primary antibodies. Then, membranes were incubated with the corresponding peroxidase-conjugated F(ab)2 fragment (Santa cruz Biotechnology Inc, Santa Cruz, CA, USA (dilution 1:5000) secondary antibodies. Immunoreactive bands were detected with the ECL Western blotting Detection Reagents Kit (Thermo Scientific Rockford USA). The relative abundance of individual proteins identified was quantified by scanning densitometry. The list of antibodies used for western-blots are provided in Table 2.

ROCK Activity Determination

We used a ROCK Activity Immunoblot Kit (Cell Biolabs, San Diego, CA, USA) that utilizes recombinant MYPT1 as a ROCK substrate. ROCK inactivates myosin phosphatase through a specific phosphorylation of myosin phosphatase target subunit 1 (MYPT1) at Thr696, which results in an increase in the phosphorylated content of the 20-kDa myosin light chain. (MLC20) After incubating the substrate (recombinant MYPT1) with RPE/choroid samples, the phosphorylated MYPT1 was detected by western blot analysis using an anti-phospho-MYPT1 (Thr696). In brief, RPE/choroid protein samples were diluted in 1× Kinase buffer. 25 µL (75 µg of proteins) was added in microcentrifuge tubes and the initiation of kinase reaction was performed by adding 50 µL of 1× Kinase/ATP/Substrate Solution. The microcentrifuge tubes were then incubated at 30° C. for 30-60 minutes with gentle agitation. Then the kinase reaction was stopped by adding 25 µL of 4× reducing SDS-PAGE sample buffer. Samples were boiled for 5 minutes and centrifuged for 10 seconds at 12,000×g. Inhibition of ROCK activity was evaluated by western blotting and quantified.

Quantitative Analysis of RPE Cell Layer Morphology

To analyse RPE flat-mounts and in order to assess the cell morphology. an ImageJ [32] macro tool was created in Fiji [33]. Briefly, after a first image processing by FFT band pass filtering, images were converted into binary format and masked and then processed to obtain a skeleton image (isolated segments and loops were removed). This image was inverted and the cells segmented and labelled with the "particle analysis" tool in ImageJ, the Regions of Interest (ROI) were delimited using ROI Manager tool. The number of vertices for each cell was measured following detection of triple points (points were three branches are joined together) with the appropriate binary "hit or miss" transformation. For this transformation, the ImageJ plugin "morphology" was used. By removing those points from the skeleton image, the number of individual edges was counted as well as their length. The number of vertices was then verified and manually corrected for errors. Images with more than 5% automatic alignment errors were eliminated from analysis. Following this several morphological parameters were then measured for each cell e.g. area, perimeter, circularity, number of neighbours/vertices/edges of a cell etc. ANOVA was used to examine if there was a statistically significant difference in the distribution of cell size between the different two models, while accounting for the multiple images taken from different animals. (linear model was: cell area model+image number+animal number).

Blood-retinal Barrier Breakdown Quantification using Intravenous Injection of FITC Dextran To assess blood retinal barrier breakdown, 200 µl of 150 KDa FITC-dextran at 50 mg/ml in PBS (Sigma) was injected intravenously in the tail of rats treated by Fasudil or vehicle (n=5), 2 hours prior killing. Leakage of FITC-dextran was evaluated by measuring fluorescence within the retina using imageJ software as previously described by others [34]. Cryosections (10 µm) of Fasudil and vehicles injected rats retina were randomly imaged (10 images at 40× magnification per animal) and analysed.

Quantitative Assessment of the Retinal Microangiopathy

To quantify the area of large and small blood vessels on flat mounted retina, an ImageJ macro was created in Fiji [32, 33]. Briefly, the local thickness function available with the Fiji plugin for ImageJ software was used to create a map of the blood vessels, from which diameter of the local structures could be evaluated. This map was thresholded to define two binary masks corresponding to the vessels of large diameter (local thickness>threshold) and the vessels of small diameter (local thickness<threshold). The area of those masks was then measured and expressed in terms of the surface area occupied by the small vessels.

Semithin and ultrathin section analysis.

Eyes from GK rats (12 months of age, n=4 rats per time point) were fixed 1 hour in 2.5% glutaraldehyde in cacodylate buffer (0.1 mol/L, pH 7.4) and then dissected, postfixed in 1% osmium tetroxide in cacodylate buffer, and dehydrated in a graded series of alcohol before being included in epoxy resin and oriented. Semithin sections (1 µm, ultramicrotome Reichert Ultracut E (Leica), were stained with toluidine blue. Ultrathin sections (80 nm) were contrasted by uranyl acetate and lead citrate and observed with a transmission electron microscope (TEM, JEOL 100 CX II (JEOL) with 80 kV) and photographed.

Statistics

For continuous variables, the mean±SD were provided. Comparisons were performed using the non-parametric, Mann-Whitney test (Prism software version 4.0c; GraphPad Software, San Diego, CA), p-values<0.05 were considered significant.

Results

Activation of ROCK-1 in Diabetes-induced Outer Blood Retinal Barrier Breakdown and RPE Cytoskeleton Remodeling.

At the apical pole of RPE cells, the F-actin filament network is intrinsically linked with and regulates tight junction (TJ) function. Visualization of the F-actin network using rhodamine phalloidin showed marked modification of RPE cell shape in the form of irregular and either constricted or enlarged cells (FIG. 1a, first row, white arrows, middle panel) with focal stress fibres (FIG. 1a, first row, upper right panel, white arrow) responsible for focal junction opening as confirmed by occludin staining (FIG. 1a second row, white arrow). ROCK-1, dispersed in the cytoplasm of non-diabetic control RPE, delocalized from the cytoplasm to the cell membrane in the RPE of diabetic rats (FIG. 1a, third row) and in the RPE of diabetic humans (FIG. 1b) indicating activation of the ROCK-1/Myosin 2 pathway, which is involved in actomyosin network constriction [19, 21].

Intra-Vitreous Injection of Fasudil Inhibits ROCK Over-Activation in RPE Cells

Figure 2D:
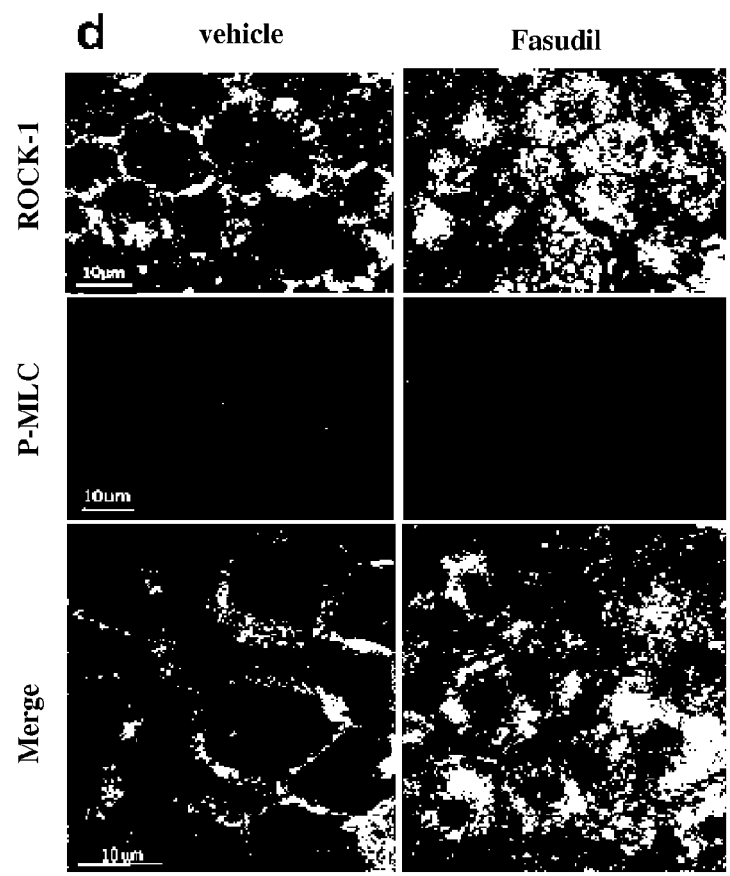

We evaluated Rho-Kinase activity on the phosphorylation state of two known substrates: MYPT1 and MLC (described in methods). The total ROCK-1 was not significantly decreased in the RPE of Fasudil treated eyes (n=6) as compared to vehicle injected eyes (n=6) (FIG. 2a). Decreased ROCK-1 activity was observed in Fasudil treated eyes, as significant reduction of phosphorylated MYTP1 and MLC in the RPE was observed of Fasudil treated eyes versus eyes receiving vehicle (FIGS. 2b and c). The ROCK substrate p-MLC is responsible for actin-myosin interaction, fiber stress formation and cell constriction. In Fasudil treated eyes a relocation of ROCK1/P-MLC from the membrane into the cytoplasm was observed, confirming that activation of both proteins was inhibited (FIG. 2d).

Fasudil Restores RPE Cell Monolayer Morphology and the Outer Retinal Barrier Breakdown Using the image processing methodology described above the composition of cells, in terms of size and formation was examined. In GK RPE flat-mounts cellular irregularities were more common with many more very large (>400 µm2) and small cells (<200 µm2) than in WS retina, overall there was a statistically significant different distribution of size of cells in the GK retina, than in the WS retina (ANOVA, p<0.001), there was no difference in distribution of cell area between the WS Fasudil and WS vehicle treated retina (ANOVA, p=0.17). In GK retina treated with Fasudil there was a reduction in the frequency of small cells and an as compared to the GK retina treated with vehicle and an increase frequency of normal size cells (FIG. 3, p<0.001).

Figure 4D:
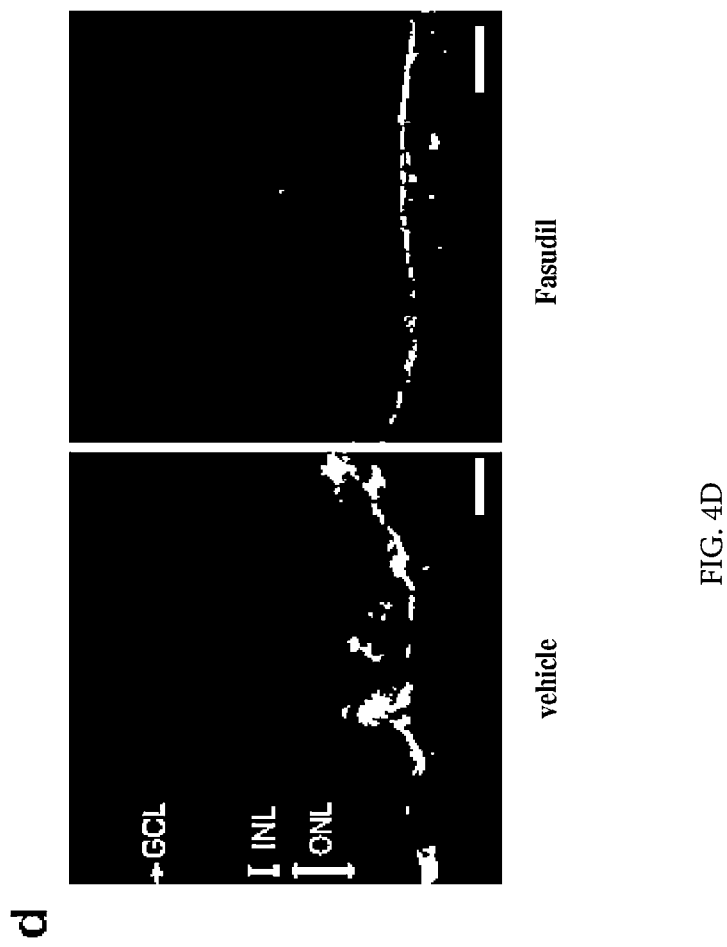
Figure 4E:
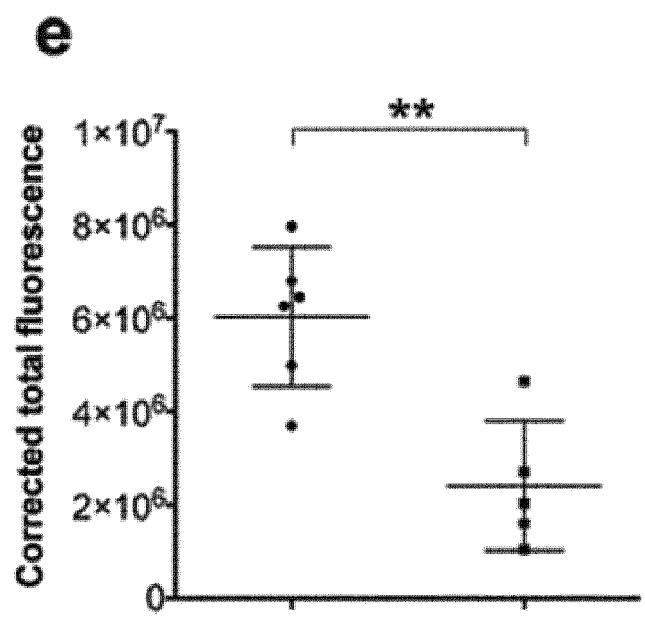

In Fasudil treated GK rats, 150 KDa FITC-dextran did not cross the RPE barrier and remained in the choroidal circulation (FIG. 3a). In vehicle-treated GK rats, FITC-labelled molecules passed though RPE breakpoints in between photoreceptor segments and nuclei (FIG. 4a, white arrows). (FIG. 4a, right panel) (FIG. 4b). On Semithin sections, enlarged extracellular spaces and increased thickness of the outer retinal layers corresponded with intraretinal oedema and the breakdown of the outer retinal barrier (FIG. 4c). In Fasudil treated GK eyes, a significant reduction in vessel leakage was observed as compared to vehicle treated eyes (FIG. 4e). On examination of the histological sections, Fasudil treated eyes demonstrated an intact RPE barrier (FIG. 4d).

ROCK is Activated in Diabetic Retinal Vessels in Rat and Human

On flat-mounted retina, phalloidin-stained actin bordered the regular diameters of retinal blood vessels in control non-diabetic rats, but showed irregular and focal constrictions of retinal vessels in diabetic rats (FIG. 5a, upper row, white arrows). Large protrusion from the vessel walls into the vessel lumen was observed (FIG. 5a, middle row, white arrows). On TEM ultrathin sections, cytoskeleton remodeling with non-apoptotic membrane blebs/protrusions were visualized, potentially corresponding to luminal protrusions (FIG. 5a, lower row, black arrow).

On flat-mounted retina of control non-diabetic rats minimal ROCK staining was detected in retinal vessels whereas in GK rats ROCK staining co-localized with actin constrictions and filled the inner vessels blebs/protrusions (FIG. 5b upper and lower row respectively). This indicates that ROCK activation contributes to the reduction of the vessel lumen diameter. Similarly in the confocal microscopy images in sections of diabetic human retinal vessels, positive staining for both ROCK1 and phalloidin around vessel wall constriction and in the vessel blebs/protrusions was observed (FIG. 5c).

Figure 6A:
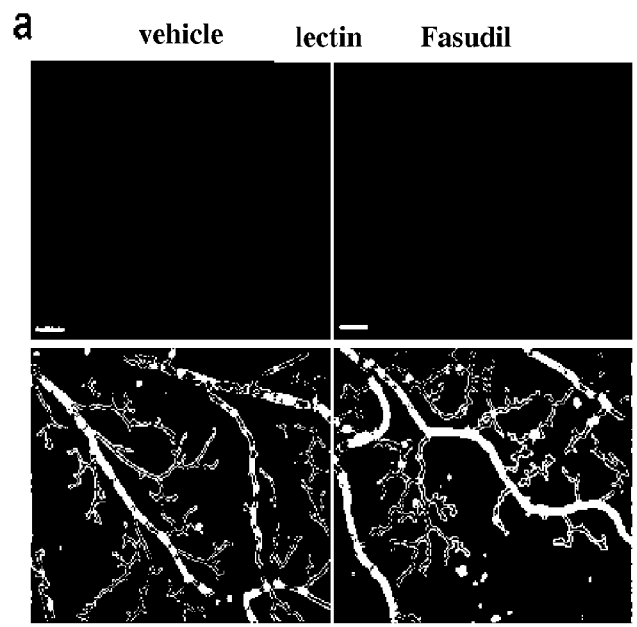
Figure 6B:
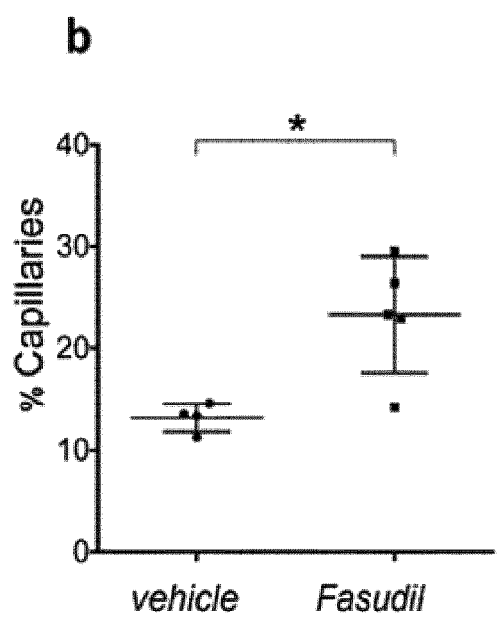

Fasudil Restores Diabetes-Induced Retinal Capillary Vasoconstriction Through Rho-Kinase Inhibition and VEGF Decrease Lectin-labelled capillary surface was quantified on flat-mounted retina of GK rats (n=4 Fasudil and n=5 vehicle) (FIG. 6a). Capillary density (expressed as % of surface coverage) was significantly increased in GK Fasudil treated eyes as compared to vehicle treated eyes (FIG. 6b). A significant decrease in VEGF levels in Fasudil treated retina was observed (western-blot; n=8/group) and on retinal flat-mounts with VEGF immunostaining (FIG. 7a), indicating a potential reduction in retinal ischemia.

Figure 8A:
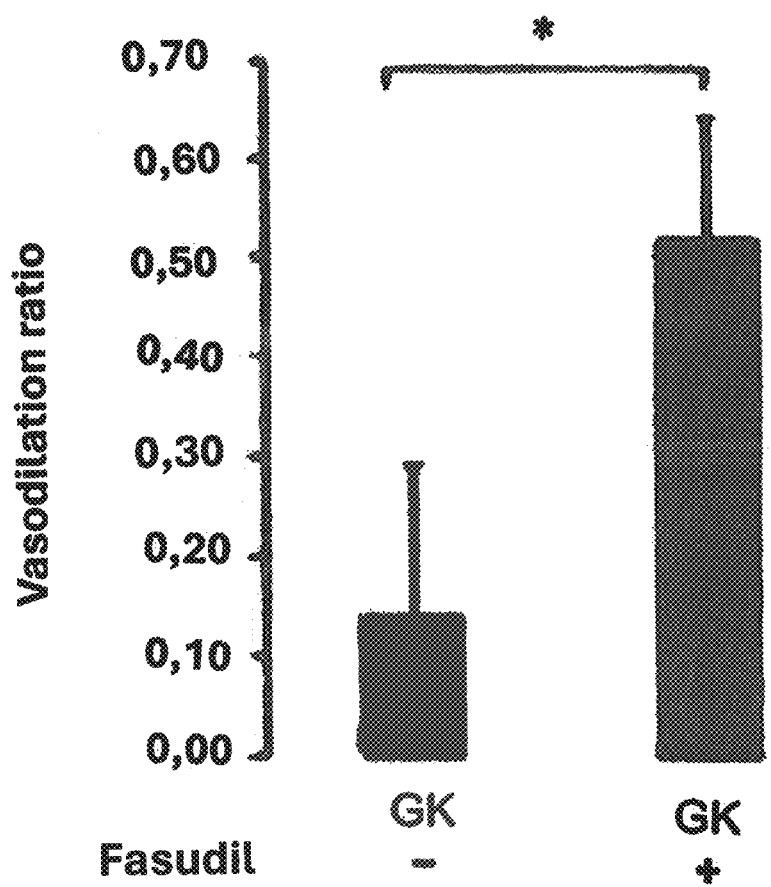
Figure 8B:
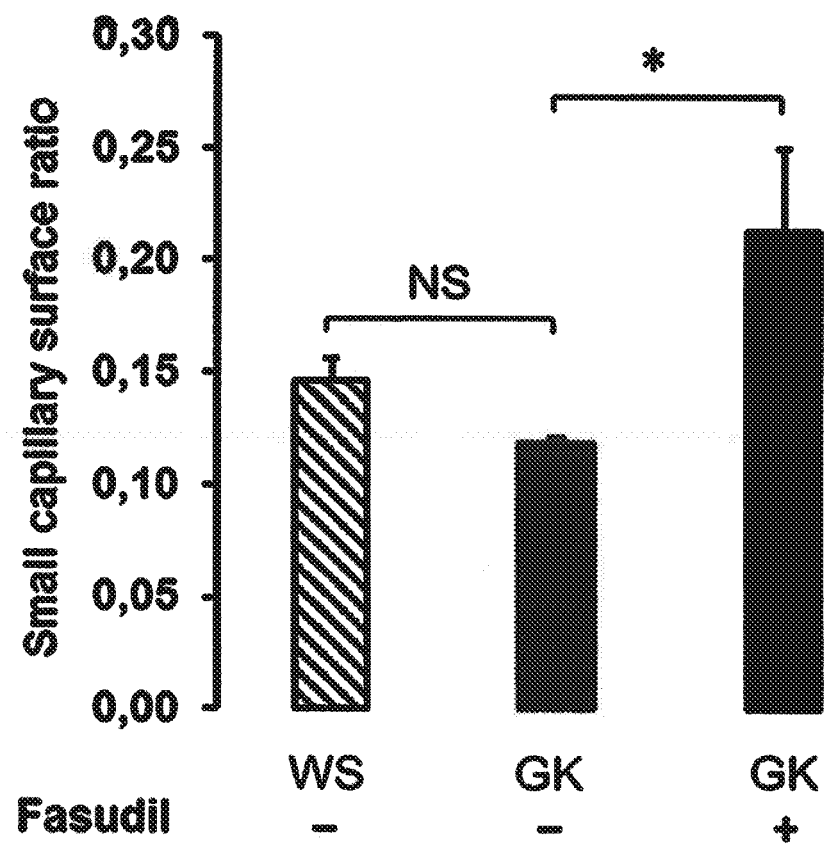
Figure 8C:
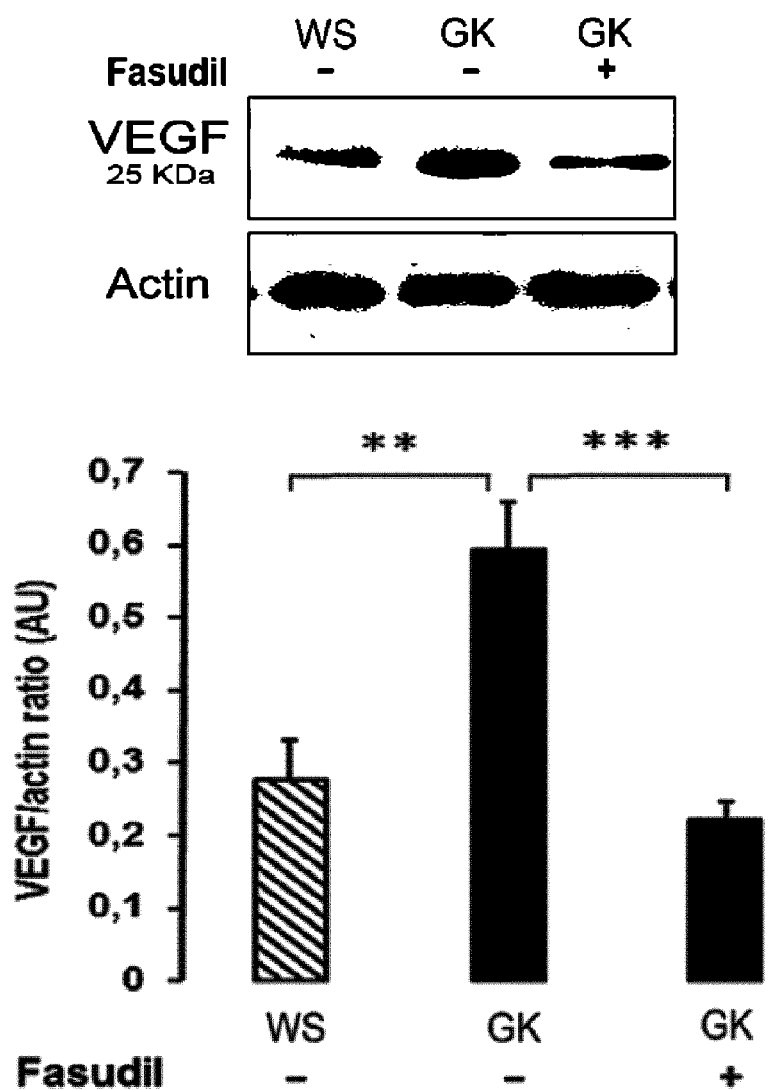

Fasudil Reduces Vasoconstriction and Improves Retinal Perfusion of the Diabetic Retina In vivo imaging of retinal vessels using confocal angiography showed that fasudil treatment induced a significant vasodilation of retinal vessels (data not shown, FIG. 8A). Furthermore; the surface of capillary coverage, assessed on retina flat-mounts stained with lectin was significantly increased in GK-fasudil treated eyes as compared to vehicle treated eyes (data not shown, FIG. 8B). Consistently, dilation of the capillary bed was associated with a significant decrease in VEGF levels (FIG. 8C) suggesting improved retinal perfusion and potentially reduced retinal ischemia.

Discussion

Using the GK rat model of diabetic retina, ROCK-1 activation in the retinal pigment epithelium/retinal vessels was shown to be associated with cytoskeletal remodeling, resulting in outer retinal barrier breakdown and retinal capillaries closure. The key role of ROCK-1 activation plays in these two processes was clearly demonstrated with the significant reduction of vessel leakage through the retinal epithelium and the marked reduction in vessel closure following the intravitreal administration of the ROCK1-inhibitor, Fasudil.

Besides the well-studied role of the inner BRB in the formation of diabetic macular oedema (DMO), mounting evidence indicates that the outer BRB plays a key role in the development of macular edema, often prior to patent diabetic retinopathy as diagnosed according to international guidelines [2]. Accumulating evidence suggest a role for the outer BRB besides the well-studied role of the inner BRB in the formation of diabetic macular edema (DME) especially in the early phases of the disease and even before any patent diabetic retinopathy as diagnosed according to international guidelines [35]. Human clinical studies have demonstrated an increase in retinal thickness correlated to HbA1C levels before the onset of DR or DME [24] and serous retinal detachments have also been described both suggesting RPE dysfunction in pre-clinical DR or DME [3, 36]. Animal studies by Xu et al. in streptozotocin injected Brown Norway rats (corresponding to diabetes type 1 model), have shown RPE tight junction alterations and leakage of FITC-Dextran molecules of less than 40 kDa starting at 9 months of diabetes duration [37]. These findings are consistent with our results in a spontaneous rat model at 12 months of age, which would correspond to diabetes duration of 9 months (diabetes onset in GK rat is approximately at 12 weeks). The observed leakage of a larger FITC-Dextran (150 KDa) molecule, may suggest greater RPE damage as compared to the T1D model of Xu et al. This is in line with an increase incidence of DME in T2D patients as compared to T1D patients in clinic.

Marked alterations of the RPE actin cytoskeleton coincided with cell shape modifications with constricted cells leading to cell-cell junction ruptures and outer BRB disruption. Chronic hyperglycaemia and the associated oxidative stress are understood to be causative in RPE membrane bleb development. This process has been previously described by Cousins et al. on RPE cells in vitro in response to chemical oxidative stress [38] but the in vivo consequences of such blebbing had not been previously examined. The role of actin cytoskeleton in the formation and regulation of cell junctions has been well studied; the role of GTPases of the Rho kinase family are essential in this being integral to this complex organization [39].

Marked alterations of the RPE actin cytoskeleton, coincided with cell shape modifications with constricted cells leading to cell-cell junction ruptures and external BRB disruption. Chronic hyperglycaemia and the associated oxidative stress is understood to be causative in RPE membrane bleb development, this process has been previously described by Cousins et al. on RPE cells in vitro in response to chemical oxidative stress [38] but the in vivo consequences of such blebbing had not been previously examined. The role of actin cytoskeleton in the formation and regulation of cell junctions has been well studied, with the role of GTPases of the Rho kinase family are essential in this being integral to this complex organization [39].

Interestingly, not only intercellular permeability but also gene transcription are regulated by the cell junction complexes. In our experiments, Fasudil treatment was associated with decreased VEGF expression in the retina. In other models, Fasudil exerted anti-angiogenic effects or reduced VEGF through mechanisms not fully elucidated [40, 41]. In endothelial cells, Fasudil was shown to inhibit hypoxia-induced HIF-1α expression and disrupt VEGF/VEGFR-2 autocrine loop [42]. The novelty of our observation is that Fasudil whilst decreasing VEGF, that is potent vasodilator enhanced the capillary density. This was achieved through a reduction of vessel constriction and of endothelial cell intraluminal blebbing, suggesting that ROCK inhibition could reduce capillary closure. Fasudil could be of high clinical interest when macular ischemia is associated macular oedema, as opposed to direct VEGF blockade that was suspected to increase ischemia in such patients [43].

The pathogenesis of capillary non-perfusion in diabetic retinopathy remains unclear. Increased leukocyte-endothelial cell adhesion and entrapment in retinal capillaries [44], endothelial dysfunction and oxidative stress [45], and vascular inflammation are recognized contributing factors [46]. The results of this article highlighting another potential mechanism in this pathogenesis, namely the activation of Rho-kinase 1, which was related to vessel lumen reduction due to the formation of membrane endothelial cell blebs [47]. The role of RhoA/ROCK1/P-MLC pathway activation has been described in membrane bleb formation of human colon cancer cells, as a response to Plasminogen Activator Inhibitor 1 (PAI-1) [48]. The PAI-1 polymorphism was recently associated with and increased risk of diabetic retinopathy and may be an activator of the ROCK pathway in the diabetic retina [49]. Blebs induced by TNF-α and combretastatin were associated with endothelial cell death in vitro, [50, 51]. Whether endothelial membrane bleb formation ultimately leads to endothelial cell death in diabetic microcirculation should be examined. The results of this study suggest that ROCK inhibition has the ability to modulate diabetic disease development and facilitates endothelial cellular morphology repair prior to irreversible retinal damage. Here ROCK inhibition with Fasudil restored cellular morphology and the RPE functional barrier in GK eyes demonstrating that cytoskeleton remodeling instigates RPE tight junction in the diabetic retina.

Fasudil (Asahi Kasei, Corp Tokyo, licensed to Shering) is the only ROCK inhibitor approved in humans in Japan for cerebral vasospasm after subarachnoid haemorrhage [52]. The potential benefit of ROCK inhibitors has been suggested in various pre-clinical models and in clinical studies for the treatment of arteriosclerosis, hypertension, pulmonary hypertension, stroke, ischemia-reperfusion injury and heart failure. But, the significant side-effects (such as convulsion, hypotension and disturbance in consciousness) due to the lack of specificity of available inhibitors have restricted clinical development [53-55].

ROCK inhibition has been also proposed in experimental diabetic nephropathy and more specific rock inhibitors are being developed to increase the possible therapeutic window [23]. In the case of intraocular administration, no systemic side-effects are expected since the eye is a confined organ with limited systemic diffusion of intraocular injected compounds.

In summary, we demonstrate that in the type 2 diabetic retina, Rho kinase 1 activation resulted in cytoskeleton remodeling and cell membrane bleb formation. In turn these contributed to the alteration of retinal barriers involved in macular oedema formation and to microvascular closure and subsequent retinal ischemia. These results indicate that intraocular ROCK inhibition is a potential molecular target for the prevention of complications associated with diabetic retinopathy.

REFERENCES

Throughout this application, various references describe the state of the art to which this invention pertains. The disclosures of these references are hereby incorporated by reference into the present disclosure.

[1] Mohamed Q, Gillies M C, Wong T Y (2007) Management of diabetic retinopathy: a systematic review. JAMA 298: 902-916
[2] Wilkinson C P, Ferris F L, Klein R E, et al. (2003) Proposed international clinical diabetic retinopathy and diabetic macular edema disease severity scales. Ophthalmology 110: 1677-1682
[3] Lobo C L, Bernardes R C, Cunha-Vaz J G (2000) Alterations of the blood-retinal barrier and retinal thickness in preclinical retinopathy in subjects with type 2 diabetes. Arch Ophthalmol 118: 1364-1369
[4] Simo R, Villarroel M, Corraliza L, Hernandez C, Garcia-Ramirez M (2010) The retinal pigment epithelium: something more than a constituent of the blood-retinal barrier—implications for the pathogenesis of diabetic retinopathy. J Biomed Biotechnol 2010: 190724
[5] Simó R, Hernández C (2015) Novel approaches for treating diabetic retinopathy based on recent pathogenic evidence. Prog Retin Eye Res
[6] Das A, McGuire P G, Rangasamy S (2015) Diabetic Macular Edema: Pathophysiology and Novel Therapeutic Targets. Ophthalmology 122: 1375-1394
[7] Riento K, Ridley A J (2003) Rocks: multifunctional kinases in cell behaviour. Nat Rev Mol Cell Biol 4: 446-456
[8] Yu W, Shewan A M, Brakeman P, et al. (2008) Involvement of RhoA, ROCK I and myosin II in inverted orientation of epithelial polarity. EMBO Rep 9: 923-929
[9] Ishiuchi T, Takeichi M (2011) Willin and Par3 cooperatively regulate epithelial apical constriction through aPKC-mediated ROCK phosphorylation. Nat Cell Biol 13: 860-866
[10] Mohan S, Das D, Bauer R J, et al. (2013) Structure of a highly conserved domain of Rock1 required for Shroom-mediated regulation of cell morphology. PLoS One 8: e81075
[11] Loirand G, Pacaud P The role of Rho protein signaling in hypertension. Nat Rev Cardiol 7: 637-647
[12] Pinterova M, Kunes J, Zicha J Altered neural and vascular mechanisms in hypertension. Physiol Res 60: 381-402
[13] Suzuki Y, Shibuya M, Satoh S, Sugimoto Y, Takakura K (2007) A postmarketing surveillance study of fasudil treatment after aneurysmal subarachnoid hemorrhage. Surg Neurol 68: 126-131; discussion 131-122
[14] Zhao J, Zhou D, Guo J, et al. (2006) Effect of fasudil hydrochloride, a protein kinase inhibitor, on cerebral vasospasm and delayed cerebral ischemic symptoms after aneurysmal subarachnoid hemorrhage. Neurol Med Chir (Tokyo) 46: 421-428
[15] Zhou Q, Gensch C, Liao J K Rho-associated coiled-coil-forming kinases (ROCKs): potential targets for the treatment of atherosclerosis and vascular disease. Trends Pharmacol Sci 32: 167-173
[16] Shibuya M, Hirai S, Seto M, Satoh S, Ohtomo E (2005) Effects of fasudil in acute ischemic stroke: results of a prospective placebo-controlled double-blind trial. J Neurol Sci 238: 31-39
[17] Connolly M J, Aaronson P I Key role of the RhoA/Rho kinase system in pulmonary hypertension. Pulm Pharmacol Ther 24: 1-14
[18] Gupta V, Gupta N, Shaik I H, et al. Liposomal fasudil, a rho-kinase inhibitor, for prolonged pulmonary preferential vasodilation in pulmonary arterial hypertension. J Control Release 167: 189-199
[19] Dong M, Yan B P, Liao J K, Lam Y Y, Yip G W, Yu C M Rho-kinase inhibition: a novel therapeutic target for the treatment of cardiovascular diseases. Drug Discov Today 15: 622-629
[20] Satoh K, Fukumoto Y, Shimokawa H Rho-kinase: important new therapeutic target in cardiovascular diseases. Am J Physiol Heart Circ Physiol 301: H287-296
[21] Pellegrin S, Mellor H (2007) Actin stress fibres. J Cell Sci 120: 3491-3499
[22] Mishra R K, Alokam R, Sriram D, Yogeeswari P (2013) Potential role of Rho kinase inhibitors in combating diabetes-related complications including diabetic neuropathy—a review. Curr Diabetes Rev 9: 249-266
[23] Komers R (2011) Rho kinase inhibition in diabetic nephropathy. Curr Opin Nephrol Hypertens 20: 77-83
[24] Komers R (2013) Rho kinase inhibition in diabetic kidney disease. Br J Clin Pharmacol 76: 551-559
[25] Guo R, Su Y, Yan J, et al. (2015) Fasudil improves short-term echocardiographic parameters of diastolic function in patients with type 2 diabetes with preserved left ventricular ejection fraction: a pilot study. Heart Vessels 30: 89-97
[26] Ahmadieh H, Nourinia R, Hafezi-Moghadam A Intravitreal fasudil combined with bevacizumab for persistent diabetic macular edema: a novel treatment. JAMA Ophthalmol 131: 923-924
[27] Kitahara A, Toyota T, Kakizaki M, Goto Y (1978) Activities of hepatic enzymes in spontaneous diabetes rats produced by selective breeding of normal Wistar rats. Tohoku J Exp Med 126: 7-11
[28] Agardh C D, Agardh E, Zhang H, Ostenson C G (1997) Altered endothelial/pericyte ratio in Goto-Kakizaki rat retina J Diabetes Complications, United States, pp 158-162
[29] Crisanti P, Laplace O, Lecain E, Jonet L, Jeanny J C, Omri B (2006) The role of PKCzeta in NMDA-induced retinal ganglion cell death:prevention by aspirin. Apoptosis 11: 983-991
[30] de Kozak Y, Omri B, Smith J R, Naud M C, Thillaye-Goldenberg B, Crisanti P (2007) Protein kinase Czeta (PKCzeta) regulates ocular inflammation and apoptosis in endotoxin-induced uveitis (EIU):signaling molecules involved in EIU resolution by PKCzeta inhibitor and interleukin-13 Am J Pathol, United States, pp 1241-1257
[31] Liang H, Baudouin C, Behar-Cohen F, Crisanti P, Omri B (2007) Protein kinase C-zeta mediates retinal degeneration in response to TNF J Neuroimmunol, Netherlands, pp 104-110
[32] Schneider C A, Rasband W S, Eliceiri K W (2012) NIH Image to ImageJ: 25 years of image analysis. Nat Methods 9: 671-675
[33] Schindelin J, Arganda-Carreras I, Frise E, et al. (2012) Fiji: an open-source platform for biological-image analysis. Nat Methods 9: 676-682
[34] Burgess A, Vigneron S, Brioudes E, Labbé J C, Lorca T, Castro A (2010) Loss of human Greatwall results in G2 arrest and multiple mitotic defects due to deregulation of the cyclin B-Cdc2/PP2A balance. Proc Natl Acad Sci USA 107: 12564-12569
[35] Yeung L, Sun C C, Ku W C, et al. (2010) Associations between chronic glycosylated haemoglobin (HbA1c) level and macular volume in diabetes patients without macular oedema. Acta Ophthalmol 88: 753-758

[36] Gaucher D, Sebah C, Erginay A, et al. (2008) Optical coherence tomography features during the evolution of serous retinal detachment in patients with diabetic macular edema. Am J Ophthalmol 145: 289-296

[37] Xu H Z, Le Y Z (2011) Significance of outer blood-retina barrier breakdown in diabetes and ischemia. Invest Ophthalmol Vis Sci 52: 2160-2164

[38] Marin-Castaño M E, Csaky K G, Cousins S W (2005) Nonlethal oxidant injury to human retinal pigment epithelium cells causes cell membrane blebbing but decreased MMP-2 activity. Invest Ophthalmol Vis Sci 46: 3331-3340

[39] Citi S, Guerrera D, Spadaro D, Shah J (2014) Epithelial junctions and Rho family GTPases: the zonular signalosome. Small GTPases 5: 1-15

[40] Zeng P, Pi R B, Li P, et al. (2015) Fasudil hydrochloride, a potent ROCK inhibitor, inhibits corneal neovascularization after alkali burns in mice. Mol Vis 21: 688-698

[41] Hata Y, Miura M, Nakao S, Kawahara S, Kita T, Ishibashi T (2008) Antiangiogenic properties of fasudil, a potent Rho-Kinase inhibitor. Jpn J Ophthalmol 52: 16-23

[42] Takata K, Morishige K, Takahashi T, et al. (2008) Fasudil-induced hypoxia-inducible factor-1alpha degradation disrupts a hypoxia-driven vascular endothelial growth factor autocrine mechanism in endothelial cells. Mol Cancer Ther 7: 1551-1561

[43] Campochiaro P A, Wykoff C C, Shapiro H, Rubio R G, Ehrlich J S (2014) Neutralization of vascular endothelial growth factor slows progression of retinal nonperfusion in patients with diabetic macular edema. Ophthalmology 121: 1783-1789

[44] Chibber R, Ben-Mahmud B M, Chibber S, Kohner E M (2007) Leukocytes in diabetic retinopathy. Curr Diabetes Rev 3: 3-14

[45] de Zeeuw P, Wong B W, Carmeliet P (2015) Metabolic adaptations in diabetic endothelial cells. Circ J 79: 934-941

[46] Semeraro F, Cancarini A, dell'Omo R, Rezzola S, Romano M R, Costagliola C (2015) Diabetic Retinopathy: Vascular and Inflammatory Disease. J Diabetes Res 2015: 582060

[47] Coleman M L, Sahai E A, Yeo M, Bosch M, Dewar A, Olson M F (2001) Membrane blebbing during apoptosis results from caspase-mediated activation of ROCK I. Nat Cell Biol 3: 339-345

[48] Cartier-Michaud A, Malo M, Charrière-Bertrand C, et al. (2012) Matrix-bound Pai-1 supports cell blebbing via RhoA/ROCK1 signaling. PLoS One 7: e32204

[49] Xu K, Liu X, Yang F, et al. (2013) PAI-1-675 4G/5G polymorphism in association with diabetes and diabetic complications susceptibility: a meta-analysis study. PLoS One 8: e79150

[50] Petrache I, Crow M T, Neuss M, Garcia J G (2003) Central involvement of Rho family GTPases in TNF-alpha-mediated bovine pulmonary endothelial cell apoptosis. Biochem Biophys Res Commun 306: 244-249

[51] Kanthou C, Tozer G M (2002) The tumor vascular targeting agent combretastatin A-4-phosphate induces reorganization of the actin cytoskeleton and early membrane blebbing in human endothelial cells. Blood 99: 2060-2069

[52] Shibuya M, Suzuki Y, Sugita K, et al. (1992) Effect of AT877 on cerebral vasospasm after aneurysmal subarachnoid hemorrhage. Results of a prospective placebo-controlled double-blind trial. J Neurosurg 76: 571-577

[53] Ishihara M, Yamanaka K, Nakajima S, Yamasaki M (2012) Intracranial hemorrhage after intra-arterial administration of fasudil for treatment of cerebral vasospasm following subarachnoid hemorrhage: a serious adverse event. Neuroradiology 54: 73-75

[54] Enomoto Y, Yoshimura S, Yamada K, Iwama T (2010) Convulsion during intra-arterial infusion of fasudil hydrochloride for the treatment of cerebral vasospasm following subarachnoid hemorrhage. Neurol Med Chir (Tokyo) 50: 7-11; discussion 11-12

[55] Tanaka K, Minami H, Kota M, Kuwamura K, Kohmura E (2005) Treatment of cerebral vasospasm with intra-arterial fasudil hydrochloride. Neurosurgery 56: 214-223; discussion 214-223

The invention claimed is:

1. A method of treating a subject suffering from or suspected of having retinal capillary non-perfusion comprising
administering locally to the subject a therapeutically effective amount of a Rho-associated protein kinase (ROCK) inhibitor to cells of a retinal pigment epithelium (RPE),
wherein the ROCK inhibitor is fasudil and is administered in an amount sufficient to reduce retinal vascular endothelial growth factor (VEGF) expression and occurrence of endothelial cell intraluminal blebbing, to at least partially restore outer blood-retinal barrier function of the RPE, and to inhibit or reduce vessel leakage through the RPE,
wherein the administering step is performed prior to development of irreversible retinal damage, and
wherein administration is intravitreous,
wherein the retinal capillary non-perfusion is secondary to preclinical diabetic retinopathy, and
wherein the retinal capillary non-perfusion is not secondary to retinal vein occlusion.

2. A method of inhibiting retinal capillary non-perfusion in a subject suffering from a disruption of an outer blood-retinal barrier, comprising
administering intravitreously to the subject a therapeutically effective amount of a Rho-associated protein kinase (ROCK) inhibitor to retinal pigment epithelial cells,
wherein the ROCK inhibitor is fasudil in an amount sufficient to inhibit or reduce loss of tight junctions between cells of a retinal pigment epithelium layer and/or to inhibit loss of the outer blood-retinal barrier function; and
wherein the administering step is performed prior to development of retinal ischemia, and wherein the fasudil reduces expression of retinal vascular endothelial growth factor and inhibits endothelial cell intraluminal blebbing;
wherein the administering step is performed prior to development of irreversible retinal damage secondary to diabetic retinopathy; and
wherein the retinal capillary non-perfusion is not secondary to retinal vein occlusion.

3. The method of claim 2, wherein the fasudil is injected intravitreously.

4. The method of claim 2, wherein the ROCK inhibitor is administered intravitreously as a biodegradable ocular implant comprising fasudil.

5. The method of inhibiting retinal capillary non-perfusion in a subject suffering from preclinical diabetic retinopathy, comprising
administering intravitreously to the subject a therapeutically effective amount of a Rho-associated protein kinase (ROCK) inhibitor to retinal pigment epithelial cells, wherein the ROCK inhibitor is fasudil and is the only active agent that is administered, wherein the therapeutically effective amount of the fasudil is sufficient to inhibit or reduce endothelial cell intraluminal blebbing, loss of tight junctions between cells of a retinal pigment epithelium layer and/or to inhibit loss of the outer blood-retinal barrier function; and wherein the administering step is performed prior to onset of diabetic retinopathy.

6. The method of claim 5, wherein the fasudil is injected intravitreously.

7. The method of claim 5, wherein the ROCK inhibitor is administered intravitreously as a biodegradable ocular implant comprising the fasudil.

* * * * *